(12) United States Patent
Raji

(10) Patent No.: US 11,518,999 B1
(45) Date of Patent: Dec. 6, 2022

(54) PLANT TRANSFORMATION

(71) Applicant: Inari Agriculture Technology, Inc., Cambridge, MA (US)

(72) Inventor: Jennifer A. Raji, Waltham, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 16/676,958

(22) Filed: Nov. 7, 2019

Related U.S. Application Data

(60) Provisional application No. 62/758,143, filed on Nov. 9, 2018.

(51) Int. Cl.
  *C12N 15/82* (2006.01)
  *C12N 5/04* (2006.01)
  *C12N 5/00* (2006.01)

(52) U.S. Cl.
  CPC ....... *C12N 15/8207* (2013.01); *C12N 5/0025* (2013.01); *C12N 5/04* (2013.01)

(58) Field of Classification Search
  None
  See application file for complete search history.

(56) References Cited

U.S. PATENT DOCUMENTS

| | | | | |
|---|---|---|---|---|
| 4,206,282 | A * | 6/1980 | Hochstein | C12Q 1/045 435/253.6 |
| 6,803,499 | B1 * | 10/2004 | Anderson | A01H 4/001 800/298 |
| 2010/0311168 | A1 | 12/2010 | Samuel et al. | |
| 2012/0023619 | A1 | 1/2012 | Samboju et al. | |
| 2013/0145488 | A1 | 6/2013 | Wang et al. | |
| 2013/0185823 | A1 | 7/2013 | Kuang et al. | |
| 2014/0096284 | A1 | 4/2014 | Martin-Ortigosa et al. | |
| 2015/0040268 | A1 | 2/2015 | Lapidot et al. | |
| 2015/0059010 | A1 | 2/2015 | Cigan et al. | |
| 2015/0082478 | A1 | 3/2015 | Cigan et al. | |
| 2015/0208663 | A1 | 7/2015 | Khodakovskaya et al. | |

OTHER PUBLICATIONS

Das, Physical methods of gene transfer: Kinetics of gene delivery into cells: A Review, Agricultural Research Communication Centre, 36 (1) 2015; 61-66 (Year: 2015).*
Golshadi, High-Efficiency Gene Transfection of Cells through Carbon Nanotube Arrays, Small Journal, 2016, 12, No. 22, 3014-3020 (Year: 2016).*
Hamada, An in planta biolistic method for stable wheat transformation, Scientific Reports, Sep. 13, 2017 (Year: 2017).*
Kamran, Alleviation of drought-induced adverse effects in spring wheat (*Triticum aestivum* L.) using proline as a pre-sowing seed treatment, Pakistan Journal of Botany, 41(2): 621-632, 2009 (Year: 2009).*
Wright, Efficient biolistic transformation of maize (*Zea mays* L.) and wheat (*Triticum aestivum* L.) using the phosphomannose isomerase gene, pmi, as the selectable marker, Plant Cell Reports, Jun. 14, 2001 (Year: 2001).*
Helenius, Gene Delivery into Intact Plants Using the Helios Gene Gun, Plant Molecular Biology Reporter 18: 287a-2871, 2000 (Year: 2000).*
Uze, Factors Influencing T-DNA Transfer from Agrobacterium to Precultured Immature Wheat Embryos (*Triticum aestivum* L.), Cereal Research Communications, vol. 28 Nos. 1-2, 2000 (Year: 2000).*
Ishida, Wheat (*Triticum aestivum* L.) Transformation Using Immature Embryos, Agrobacterium Protocols, Sep. 13, 2014. (Year: 2014).*
Lonsdale, Transient Expression of Exogenous DNA in Intact, Viable Wheat Embryos Following Particle Bombardment, Journal of Experimental Botany, 1990 (Year: 1990).*
Upadhyay, RNA-Guided Genome Editing for Target Gene Mutations in Wheat, G3: Genes, Genomes, and Genetics, vol. 3, Dec. 2013 (Year: 2013).*
MS medium for *Arabidopsis*, Cold Spring Harbor Protocols, 2010 (Year: 2010).*
Burgess, Murashige and Skoog (MS) agar, Protocols.io, 2019 (Year: 2019).*
Marino, Comparative effects of sorbitol and sucrose as main carbon energy sources in micropropagation of apricot, Plant Cell, Tissue and Organ Culture, 1993 (Year: 1993).*
Lowe, Rapid genotype "independent" *Zea mays* L. (maize) transformation via direct somatic embryogenesis, In Vitro Cellular & Developmental Biology—Plant, Apr. 30, 2018 (Year: 2018).*
Lowe, Morphogenic Regulators Baby boom and Weichel Improve Monocot Transformation, The Plant Cell, Sep. 2016 (Year: 2016).*
Randolph-Anderson et al., "Sub-micron gold particles are superior to larger particles for efficient Biolistic® transformation of organelles and some cell types", BIO-RAD, US/EG Bulletin, pp. 1-4, 2015.
Stelpflug et al., "Consistent and Heritable Alterations of DNA Methylation are Induced by Tissue Culture in Maize", Genetics, vol. 198, pp. 209-218, Sep. 2014.
Stroud et al., "Plants regenerated from tissue culture contain stable epigenome changes in rice", eLIFE, elifesciences.org research article, https://elifesciences.org/articles/00354, 25 pages 2013.

* cited by examiner

*Primary Examiner* — Amjad Abraham
*Assistant Examiner* — Brian James Sullivan
(74) *Attorney, Agent, or Firm* — McKee, Voorhees & Sease, PLC

(57) ABSTRACT

Compositions and methods useful for plant transformation without employing selection and without requiring tissue culture through a callus stage are provided. Transformed monocot plants can be obtained with the compositions and methods.

20 Claims, 3 Drawing Sheets
(3 of 3 Drawing Sheet(s) Filed in Color)

PLANT TRANSFORMATION

REFERENCE TO RELATED APPLICATIONS

This application claims benefit of priority to U.S. Provisional Patent Application No. 62/758,143 filed 9 Nov. 2018, and incorporated herein by reference in its entirety.

FIELD

Aspects of this disclosure relate to biotechnology, in particular compositions and methods for plant transformation.

BACKGROUND

Methods of modifying plant genomes by introducing a transgene or by targeted editing (e.g., using nucleases such as zinc-finger nucleases (ZFNs), transcription activator-like effector nucleases (TAL-effector nucleases or TALENs), and RNA-guided nucleases such as CRISPR Cas nucleases) generally have relied on transforming plant material using techniques such as *Agrobacterium*-mediated transformation or particle-mediated transformation (Biolistics). These transformation methods typically require subjecting the transformed plant material or explants to tissue culture through a dedifferentiated callus phase, and often involve selection with an antibiotic or herbicide (thus requiring the corresponding antibiotic or herbicide resistance transgene to be incorporated into the transformed plant). See, e.g., Gordon-Kamm et al. (1990) *Plant Cell,* 2:603-618. Transformed plants that contain an introduced transgene for such selection are generally subject to stringent regulatory requirements. Removal of such an introduced transgene generally requires at least one crossing or backcrossing step, which itself can introduce unwanted genomic changes in the resulting progeny plants.

Plant tissue culture as used in the production of transformed plants results in significant changes (typically a decrease) in genome methylation status and heritable epigenome changes in the resulting transformed plants; this may lead to unintended phenotypic changes or unwanted somaclonal variation in the resulting transformed plants. See, e.g., Stroud et al. (2013) eLife 2:e00354; DOI:10.7554/eLife.00354; Stelpflug et al. (2014) *Genetics,* 198:209-218. Furthermore, crop plants such as maize are often commercially provided as "elite germplasm", or inbred lines that have been selectively bred and optimized for a given growing condition or region; not all germplasm or inbred lines are equally amenable to transformation using tissue culture.

For at least the above reasons, methods of plant transformation that do not require use of selection or tissue culture through a callus stage are advantageous.

SUMMARY

Disclosed herein are compositions and methods useful for plant transformation without employing selection and without requiring tissue culture through a callus stage.

In one aspect, the invention provides a method of providing a transformed monocot plant, the method including the steps of: (a) contacting an explant comprising meristem tissue of a source monocot plant with a hypertonic medium that comprises MES salt and L-proline, and that does not comprise a growth hormone, an antioxidant, silver nitrate, or a selection agent, for an amount of time sufficient to reduce turgor in the meristem tissue; (b) bombarding the meristem tissue with transformation carriers complexed with at least one transformation agent, wherein the transformation carriers are delivered: (i) at between about 60-about 400 psi with a hand-held biolistic particle delivery system at atmospheric pressure, or (ii) using a rupture disk of less than 1100 psi with a benchtop biolistic particle delivery system under vacuum; (c) contacting the bombarded monocot meristem tissue with the hypertonic medium, for at least about 4 hours; and (d) regenerating plantlets on a base medium that does not comprise a growth hormone, an antioxidant, silver nitrate, or a selection agent, without transition through a callus phase; whereby a transformed monocot plant that includes germline cells having multiple genetic modifications effected by the transformation agent is regenerated without the use of a selection agent and without transition through a callus phase. The method is useful in plants including monocots, such as grasses, the family Poaceae (Gramineae), and especially grain crop species used as food or feed (e.g. wheat, maize, rice, barley, millet, and *sorghum*). The method can be used in elite germplasm that may be recalcitrant to transformation methods requiring tissue culture involving a callus phase. In embodiments, the explant includes meristem tissue, made at least partially accessible or exposed to bombardment by removal of adjacent non-meristematic tissue. In embodiments, the meristem tissue is kept continually hydrated, e.g., by continual or near-continual contact with a liquid such as water or an aqueous medium. In a pre-bombardment step, the explant is contacted with a liquid, gel, or solid "osmotic" or hypertonic medium; in embodiments this contacting with the hypertonic medium is carried out for an amount of time sufficient to reduce turgor in the meristem tissue. In many embodiments, the method employs a single bombardment of the explant, in contrast to methods where an explant is bombarded multiple times; in these embodiments, whether using a benchtop biolistic particle delivery system under vacuum, or a hand-held biolistic particle delivery system used at atmospheric pressure, bombarding is performed only once on the explant. Furthermore, the single bombardment is performed using relatively low bombardment pressure, e.g., at between about 60-about 400 psi with a hand-held biolistic particle delivery system, or using a rupture disk of less than 1100 psi with a benchtop biolistic particle delivery system. This combination of only a single bombardment and low bombardment pressure differs significantly from bombardment methods that employ multiple bombardment "shots" at higher pressures, e.g., 1100 psi or greater with a benchtop biolistic particle delivery system. After bombardment, the bombarded monocot meristem tissue is contacted with a hypertonic medium, for at least about 4 hours; this hypertonic medium can be the same as, or different from, the hypertonic medium that is used in the pre-bombardment step (for convenience it is the same), and includes MES salt and L-proline but does not include any of a number of components that are frequently used in plant tissue culture, such as a growth hormone, an antioxidant, silver nitrate, or a selection agent. Plantlets are then regenerated directly from the bombarded explant, on a base medium that does not include a growth hormone, an antioxidant, silver nitrate, or a selection agent, and without transition through a callus phase. A transformed monocot plant or plantlet that includes germline cells having multiple genetic modifications effected by the transformation agent is thus regenerated without the use of a selection agent and without transition through a callus phase.

The method is useful for delivering various transformation agents, including, but not limited to, polynucleotides, polypeptides, and combinations thereof. In embodiments, transformation efficiencies (measured as the number of surviving explants exhibiting at least one transformed cell or explant area, divided by the total number of explants subjected to bombardment, expressed as a percentage) achieved using the method are at least 85%, and preferably at least 90%, at least 95%, or even greater than 95%. The method provides a regenerated transformed ("T0") monocot plant containing at least one genetic modification effected by the transformation agent that is absent in the source monocot plant; depending on the transformation agents used, the genetic modification can be variously characterized as transient transformation, stable genomic changes, gene editing, base editing; single or multiplexed genetic changes. For example, in embodiments of the method, the transformation agent includes an RNA-guided nuclease, and the T0 plant contains a genome that has been edited by the RNA-guided nuclease; examples of such "genome editing" include deletion of one or more nucleotides, insertion of one or more nucleotides, insertion of a nucleotide sequence encoded by a donor polynucleotide, allele substitution or replacement, and combinations of such genomic changes. Related aspects of the invention include a regenerated transiently or stably transformed monocot plant produced by the method described above. In embodiments, the regenerated transformed monocot plant has a genome that is greater than 99.9% identical to that of the source monocot plant. Because the method does not require tissue culture through a callus phase, the T0 plant (and progeny T1 seeds or T1 plants) do not exhibit the degree of epigenetic changes (such as hypomethylation) that is observed in transformed plants that are produced using tissue culture through a callus phase.

Generally, the method provides a regenerated transformed ("T0") monocot plant that is fertile. The method often further includes the step of recovering T1 seeds from the transformed monocot plant, and optionally growing a progeny transformed monocot plant from the T1 seed. In embodiments, the T1 seeds obtained from a single transformed monocot plant individually include one of at least two T1 genomes that differ from each other in their genetic modifications, relative to the genome of the source monocot plant; in other words, a given germline cell in a single T0 plant can differ from another germline cell in the same plant in terms of the genetic modifications effected by the transformation agent. This means that, from a single T0 plant, T1 seeds having a multiplicity of genotypes can be obtained.

Related aspects of the invention include the regenerated transformed ("T0") monocot plant, T1 seeds obtained from the T0 plant, T1 progeny plants grown from the T1 seeds, and progeny thereof, including hybrid progeny plants of later generations. Also encompassed by the invention are raw plant materials, processed plant products, and commodity plant products obtained from a T1 plant, T1 plant cell, T1 plant tissue, or T1 seed (or from progeny plants or seeds thereof).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1.

FIG. 1B, right panel illustrates enlarged fluorescence micrographs of two transformed wheat meristems, showing intense and wide-spread GFP expression, indicating successful transformation of a large proportion of the meristem L2 cell layer.

DETAILED DESCRIPTION OF THE INVENTION

Figure 1A:
FIG. 1A illustrates a brightfield micrograph of a typical plate holding wheat explants (apical shoot meristems) arranged in a grid for bombardment as described in detail in Example 3.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art. Where a term is provided in the singular, the inventors also contemplate aspects of the invention described by the plural of that term.

By "polynucleotide" is meant a nucleic acid molecule containing multiple nucleotides and refers to "oligonucleotides" (defined here as a polynucleotide molecule of between 2-25 nucleotides in length) and polynucleotides of 26 or more nucleotides. Polynucleotides are generally described as single- or double-stranded. Where a polynucleotide contains double-stranded regions formed by intra- or intermolecular hybridization, the length of each double-stranded region is conveniently described in terms of the number of base pairs. Aspects of this invention include the use of polynucleotides or compositions containing polynucleotides; embodiments include one or more oligonucleotides or polynucleotides or a mixture of both, including single- or double-stranded RNA or single- or double-stranded DNA or double-stranded DNA/RNA hybrids or chemically modified analogues or a mixture thereof. In various embodiments, a polynucleotide includes a combination of ribonucleotides and deoxyribonucleotides (e. g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides), or includes non-canonical nucleotides such as inosine, thiouridine, or pseudouridine. In embodiments, the polynucleotide includes chemically modified nucleotides (see, e. g., Verma and Eckstein (1998) *Annu. Rev. Biochem.*, 67:99-134); for example, the naturally occurring phosphodiester backbone of an oligonucleotide or polynucleotide can be partially or completely modified with phosphorothioate, phosphorodithioate, or methylphosphonate internucleotide linkage modifications; modified nucleoside bases or modified sugars can be used in oligonucleotide or polynucleotide synthesis; and oligonucleotides or polynucleotides can be labelled with a fluorescent moiety (e. g., fluorescein or rhodamine or a fluorescence resonance energy transfer or FRET pair of chromophore labels) or other label (e. g., biotin or an isotope). Modified nucleic acids, particularly modified RNAs, are disclosed in U.S. Pat. No. 9,464,124, incorporated by reference in its entirety herein.

"CRISPR (Clustered Regularly Interspaced Short Palindromic Repeats)/Cas (CRISPR-associated) systems," or CRISPR systems, are adaptive defense systems originally discovered in bacteria and archaea. CRISPR systems use RNA-guided nucleases termed CRISPR-associated or "Cas"

endonucleases (e.g., Cas9 or Cas12a ("Cpf1")) to cleave foreign DNA. In a typical CRISPR/Cas system, a Cas endonuclease is directed to a target nucleotide sequence (e.g., a site in the genome that is to be sequence-edited) by sequence-specific, non-coding "guide RNAs" that target single- or double-stranded DNA sequences. In microbial hosts, CRISPR loci encode both Cas endonucleases and "CRISPR arrays" of the non-coding RNA elements that determine the specificity of the CRISPR-mediated nucleic acid cleavage.

Two classes (1 and 2) of CRISPR systems have been identified across a wide range of bacterial hosts. The well characterized class 2 CRISPR systems use a single Cas endonuclease (rather than multiple Cas proteins). One class 2 CRISPR system includes a type II Cas endonuclease such as Cas9, a CRISPR RNA ("crRNA"), and a trans-activating crRNA ("tracrRNA"). A "trans-activating crRNA" or "tracrRNA" is a trans-encoded small RNA that is partially homologous to repeats within a CRISPR array. At least in the case of Cas9 type CRISPR systems, both a tracrRNA and a crRNA are required for the CRISPR array to be processed and for the nuclease to cleave the target DNA sequence. In contrast, Cas12a type CRISPR systems have been reported to function without a tracrRNA, with the Cas12a CRISPR arrays processed into mature crRNAs without the requirement of a tracrRNA; see Zetsche et al. (2015) Cell, 163: 759-771 and U.S. Pat. No. 9,790,490. The Cas9 crRNA contains a "spacer sequence", typically an RNA sequence of about 20 nucleotides (in various embodiments this is 20, 21, 22, 23, 24, 25, or up to about 30 contiguous nucleotides in length) that corresponds to (e.g., is identical or nearly identical to, or alternatively is complementary or nearly complementary to) a target DNA sequence of about equivalent length. The Cas9 crRNA also contains a region that binds to the Cas9 tracrRNA to form a partially double-stranded structure which is cleaved by RNase III, resulting in a crRNA:tracrRNA hybrid or duplex. The crRNA:tracrRNA hybrid then directs the Cas9 endonuclease to recognize and cleave the target DNA sequence; in some examples, a tracrRNA and crRNA (e.g., a crRNA including a spacer sequence) can be included in a chimeric nucleic acid referred to as a "single guide RNA" (sgRNA).

The Cas12a ("Cpf1") CRISPR system includes the type V endonuclease Cas12a (also known as "Cpf1"). Cas12a nucleases are characterized as having only a RuvC nuclease domain, in contrast to Cas9 nucleases which have both RuvC and HNH nuclease domains. Cas12a nucleases are generally smaller proteins than Cas9 nucleases, and can function with a smaller guide RNA (e.g., a crRNA having at least one spacer flanked by direct repeats), which are practical advantages in that the nuclease and guide RNAs are more economical to produce and potentially more easily delivered to a cell. Examples of Cas12a nucleases include AsCas12a or "AsCpf1" (from *Acidaminococcus* sp.) and LbCas12a or "LbCpf1" (from Lachnospiraceae bacteria). In contrast to Cas9 type CRISPR systems, Cas12a-associated ("Cpf1"-associated) CRISPR arrays have been reported to be processed into mature crRNAs without the requirement of a tracrRNA, i.e., the naturally occurring Cas12a (Cpf1) CRISPR system was reported to require only the Cas12a (Cpf1) nuclease and a Cas12a crRNA to cleave the target DNA sequence; see Zetsche et al. (2015) Cell, 163:759-771; U.S. Pat. No. 9,790,490.

The genomic DNA sequence targeted for editing or modification must generally be adjacent to a "protospacer adjacent motif" ("PAM") that is specific for a given Cas endonuclease; however, PAM sequences are short and relatively non-specific, appearing throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). Some endonucleases, e.g., Cas9 endonucleases, are associated with G-rich PAM sites, e.g., 5'-NGG, and perform blunt-end cleaving of the target DNA at a location three nucleotides upstream from (5' from) the PAM site. Cas12a (Cpf1) CRISPR systems cleave the target DNA adjacent to a short T-rich PAM sequence, e.g., 5'-TTN, in contrast to the G-rich PAM sequences identified for Cas9 systems. Examples of Cas12a PAM sequences include those for the naturally occurring *Acidaminococcus* sp. BV3L6 Cpf1 (AsCpf1) and Lachnospiraceae bacterium ND2006 Cpf1 (LbCpf1) TTTV, where V can be A, C, or G. In some instances, Cas12a can also recognize a 5'-CTA PAM motif. Cas12a cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al. (2015) Cell, 163:759-771.

For the purposes of gene editing, CRISPR arrays can be designed to contain one or multiple guide RNAs designed to target a DNA sequence for editing, where the guide RNA includes at least one spacer sequence that corresponds to a specific locus of about equivalent length in the target DNA; see, for example, Cong et al. (2013) Science, 339:819-823; Ran et al. (2013) Nature Protocols, 8:2281-2308. As used herein "guide RNA" or "gRNA" refers to a nucleic acid that comprises or includes a nucleotide sequence (sometimes referred to a "spacer sequence") that corresponds to (e.g., is identical or nearly identical to, or alternatively is complementary or nearly complementary to) a target DNA sequence (e.g., a contiguous nucleotide sequence that is to be modified) in a genome; the guide RNA functions in part to direct the CRISPR nuclease to a specific location on the genome. In embodiments, a gRNA is a CRISPR RNA ("crRNA"). For nucleases (such as a Cas9 nuclease) that require a combination of a trans-activating crRNA ("tracrRNA") and a crRNA for the nuclease to cleave the target nucleotide sequence, the gRNA can be a tracrRNA:crRNA hybrid or duplex, or can be provided as a single guide RNA (sgRNA). At least 16 or 17 nucleotides of gRNA sequence corresponding to a target DNA sequence are required by Cas9 for DNA cleavage to occur; for Cas12a (Cpf1) at least 16 nucleotides of gRNA sequence corresponding to a target DNA sequence are needed to achieve detectable DNA cleavage and at least 18 nucleotides of gRNA sequence corresponding to a target DNA sequence were reported necessary for efficient DNA cleavage in vitro; see Zetsche et al. (2015) Cell, 163:759-771. Cas12a (Cpf1) endonuclease and corresponding guide RNAs and PAM sites are disclosed in U.S. Pat. No. 9,790,490, which is incorporated herein by reference in its entirety and particularly for its disclosure of DNA encoding Cas12a (Cpf1) endonucleases and guide RNAs and PAM sites. In practice, guide RNA sequences are generally designed to contain a spacer sequence of between 17-24 contiguous nucleotides (frequently 19, 20, or 21 nucleotides) with exact complementarity (e.g., perfect base-pairing) to the targeted gene or nucleic acid sequence; guide RNAs having spacers with less than 100% complementarity to the target sequence can be used (e.g., a gRNA with a spacer having a length of 20 nucleotides and between 1-4 mismatches to the target sequence), but this can increase the potential for off-target effects. The design of effective guide RNAs for use in plant genome editing is disclosed in US Patent Application Publication 2015/0082478 A1, the entire specification of which is incorporated herein by reference. Chemically modified sgRNAs have been demonstrated to be effective in Cas9 genome editing; see, for example, Hendel et al. (2015) *Nature Biotechnol.*, 33:985-991.

CRISPR-type genome editing has value in various aspects of agriculture research and development. CRISPR elements, e.g., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas12a-type endonuclease or combinations with unique PAM recognition sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cas12a (Cpf1) endonuclease and corresponding guide RNAs and PAM sites are disclosed in U.S. Pat. No. 9,790,490 and U.S. patent application Ser. No. 15/566,528 (national phase of PCT Application PCT/EP2016/058442, published as WO 2016/166340). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

Endonucleases including RNA-guided nucleases such as Cas9 and Cas12a (Cpf1) can be provided to a cell in different forms. In an embodiment, an endonuclease is provided as a ribonucleoprotein (RNP) complex, e. g., a preassembled RNP that includes the endonuclease complexed with a polynucleotide including the gRNA or encoding a gRNA, or a preassembled RNP that includes a polynucleotide that encodes the endonuclease (and optionally encodes the gRNA, or is provided with a separate polynucleotide including the gRNA or encoding a gRNA), complexed with a protein. In embodiments, the endonuclease is a fusion protein, i.e., wherein the endonuclease is covalently bound through a peptide bond to a cell-penetrating peptide, a nuclear localization signal peptide, a chloroplast transit peptide, or a mitochondrial targeting peptide; such fusion proteins are conveniently encoded in a single nucleotide sequence, optionally including codons for linking amino acids. In embodiments, the endonuclease or a polynucleotide that encodes the endonuclease is provided as a complex with a cell-penetrating peptide or other transfecting agent. In embodiments, the endonuclease or a polynucleotide that encodes the endonuclease is complexed with, or covalently or non-covalently bound to, a further element, e. g., a carrier molecule, an antibody, an antigen, a viral movement protein, a polymer, a detectable label (e. g., a moiety detectable by fluorescence, radioactivity, or enzymatic or immunochemical reaction), a quantum dot, or a particulate or nanoparticulate. In embodiments, the endonuclease or a polynucleotide that encodes the endonuclease is provided in combination with further elements (e. g., a carrier molecule, an antibody, an antigen, a viral movement protein, a polymer, a detectable label, a quantum dot, or a particulate or nanoparticulate).

In certain embodiments, at least one double-stranded break (DSB) is effected at a precisely determined site in the plant genome, for example by means of an RNA-guided nuclease and guide RNAs, and a nucleotide sequence encoded by a donor polynucleotide is heterologously integrated at the site of the DSB (or between two DSBs). In embodiments, the donor polynucleotide includes single-stranded DNA, optionally including chemical modifications. In other embodiments, the donor polynucleotide includes double-stranded DNA, optionally including chemical modifications. In some embodiment the donor polynucleotide includes both DNA and RNA, for example as a duplex formed by a DNA strand and an RNA strand. In embodiments, the donor polynucleotide is designed to include a template for genome editing via homology-dependent repair (HDR); the template generally includes a "core sequence" that is to replace a sequence of the genome of about the same size, as well as "homology arms" that flank the core sequence on either side and have a sequence complementary to the genomic regions flanking the genomic sequence to be replaced or edited. In other embodiments, the donor polynucleotide does not include homology arms or does not include a core sequence and homology arms, for example in embodiments where the donor polynucleotide is used to make a deletion.

In general, a donor polynucleotide including a template encoding a nucleotide change over a region of less than about 50 nucleotides is conveniently provided in the form of single-stranded DNA; larger donor templates (e.g., more than 100 nucleotides) are often conveniently provided as double-stranded DNAs. Thus in some embodiments, the donor polynucleotide is about 25 nucleotides, 50 nucleotides, 60 nucleotides, 70 nucleotides 80 nucleotides, 90 nucleotides, 100 nucleotides, 200 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1500 nucleotides, 1800 nucleotides, 2000 nucleotides, 2500 nucleotides, 3000 nucleotides, 5000 nucleotides, 10,000 nucleotides, or more (such as about 25-200 nucleotides, 50-300 nucleotides, 100-500 nucleotides, 200-800 nucleotides, 700-2000 nucleotides, 1000-

2500 nucleotides, 2000-5000 nucleotides, 4000-8000 nucleotides, or 6000-10,000 nucleotides).

The term "heterologous" describes a nucleic acid sequence that is positioned out of its naturally occurring or native context; the term also describes two adjacent nucleic acid sequences that do not naturally occur together (but are not necessarily from different species). The term "heterologous" is also used to refer to a given sequence in relationship to another—e.g., the sequence of a donor polynucleotide molecule is heterologous to the sequence of the genomic locus wherein the polynucleotide is integrated. For example, a ubiquitin promoter sequence can be used to drive expression of a gene (for example, luciferase) other than the ubiquitin gene natively driven by the promoter; in this case the ubiquitin promoter is "heterologous" to the luciferase gene (and vice versa), and the ubiquitin promoter and luciferase gene are in a heterologous arrangement relative to each other. In an example in bread wheat (an allohexaploid having an A, B, and D genome), a transcription factor binding site sequence that natively occurs only in the A genome of bread wheat is "heterologously" integrated into the B genome of bread wheat; this integration of a cis-genic sequence is also termed heterologous, and the resulting combined sequences of the A genome transcription factor binding site sequence and B genome sequence are a heterologous arrangement. By "integration of heterologous sequence" is also meant integration or insertion of one or more nucleotides, resulting in a sequence (including the inserted nucleotide(s) as well as at least some adjacent nucleotides of the genomic sequence flanking the site of insertion at the DSB that is itself heterologous, i.e., would not otherwise or does not normally occur at the site of insertion.

By "capable of specifically binding to" is meant an agent that binds substantially or preferentially only to a defined target (such as an oligonucleotide or polynucleotide to a specific nucleic acid). In some examples, an oligonucleotide or polynucleotide capable of specifically binding to a target nucleic acid is complementary to the target nucleic acid. However, exact complementarity is not required for specific binding.

By "complementary" is meant sequences with at least sufficient complementarity to permit enough base-paring for two nucleic acids to hybridize (for example, for a tether to hybridize with or bind to a gRNA or donor DNA), which in some examples may be under typical physiological conditions for the cell. In some examples, the oligonucleotide or polynucleotide is at least 80% complementary to the target, for example, at least 85%, 90%, 95%, 96%, 97%, 98%, 99%, or 100% complementary to the target.

By "complex" is meant two or more associated components, such as two or more associated nucleic acids and/or proteins. A complex may include two or more covalently linked nucleic acids and/or proteins, two or more non-covalently linked nucleic acids and/or proteins, or a combination thereof. In an example, a complex includes a nuclease (such as a Cas12a nuclease) and an appropriate crRNA; such a complex can optionally include one or more polynucleotides, such as the tracrRNA molecules described herein, donor polynucleotides, and functional RNA moieties. In some examples, a complex includes a gRNA (such as a crRNA) and a donor polynucleotide (or a template for production of a donor polynucleotide), which may be covalently or non-covalently linked. In other examples, a complex includes a nuclease and a donor DNA, which may be covalently linked. In further example, a complex includes one or more CRISPR nuclease polypeptides, a gRNA, and a donor DNA (or a template for production of donor DNA).

By "covalently linked" is meant that two elements (such as a gRNA and a tether or a gRNA and a donor DNA) are joined by a covalent bond, for example, an internucleotide linkage such as a phosphodiester bond, a phosphorothioate bond, a phosphothioate bond, or a peptide bond.

By "non-covalently linked" is meant that two elements (such as two discrete polynucleotides, or a polypeptide and a polynucleotide) interact non-covalently, for example by hydrogen bonding, such as Watson-Crick base pairing. Other non-covalent interactions include non-Watson-Crick pairing, electrostatic interactions, van der Waals forces, π-effects, and hydrophobic effects.

Method of Providing a Transformed Monocot Plant

An aspect of this invention provides a method of providing a transformed monocot plant, the method including the steps of: (a) contacting an explant comprising meristem tissue of a source monocot plant with a hypertonic medium that comprises MES salt and L-proline, and that does not comprise a growth hormone, an antioxidant, silver nitrate, or a selection agent, for an amount of time sufficient to reduce turgor in the meristem tissue; (b) bombarding the meristem tissue with transformation carriers complexed with at least one transformation agent, wherein the transformation carriers are delivered: (i) at between about 60-about 400 psi with a hand-held biolistic particle delivery system at atmospheric pressure, or (ii) using a rupture disk of less than 1100 psi with a benchtop biolistic particle delivery system under vacuum; (c) contacting the bombarded monocot meristem tissue with the hypertonic medium, for at least about 4 hours; and (d) regenerating plants or plantlets on a base medium that does not comprise a growth hormone, an antioxidant, silver nitrate, or a selection agent, without transition through a callus phase; whereby a transformed monocot plant that includes germline cells having multiple genetic modifications effected by the transformation agent is regenerated without the use of a selection agent and without transition through a callus phase.

In embodiments, the monocot plant is from the family Poaceae (Gramineae). In embodiments, the monocot plant is a grain crop species, for example, any of the many varieties of wheat, maize, rice, barley, millet, and sorghum. In embodiments, the monocot plant is selected from the group consisting of common or bread wheat (*Triticum aestivum*), spelt (*Triticum spelta*), emmer (*Triticum dicoccum*), einkorn (*Triticum monococcum*), durum wheat (*Triticum turgidum* or *Triticum durum*), or synthetic hexaploid wheat. Because the method can be used in various germplasms and employs no selectable marker or other transgene that requires crossing or backcrossing to eliminate the marker or transgene in progeny generations, the method is particularly useful in elite germplasm of a grain crop species, or in an inbred line of a grain crop species.

The method employs an explant comprising meristem tissue of a source monocot plant. In embodiments, the meristem tissue includes shoot apical, root apical, nodal, or auxiliary meristem tissue. In embodiments, the meristem tissue includes meristem tissue in an embryo, seedling or plantlet, or plant. In embodiments, the explant includes a monocot meristem tissue that is partially or wholly accessible/exposed to bombardment. In an example, the explant includes a monocot embryonic shoot apical meristem tissue that is made partially or wholly accessible or exposed to the transformation carriers during bombardment. In an example, the meristem tissue includes shoot apical meristem made accessible for bombardment by removal of all embryonic leaf material. Generally, in the practice of the method, the meristem tissue is kept continually hydrated, e.g., by continual or near-continual contact with a liquid such as water or an aqueous medium. The meristem tissue may be briefly removed from immediate contact with a liquid during the dissection process, but it should be kept moist.

In particular embodiments of the method, the monocot plant is wheat, and the explant includes embryonic shoot apical meristem prepared from mature wheat seed that has been subjected to imbibition. In other embodiments of the method, the monocot plant is maize, and wherein the explant includes shoot apical meristem; in embodiments, the shoot apical meristem is prepared by microdissection of: (a) immature maize embryos, (b) mature maize embryos, (c) germinating maize embryos, (d) maize seedlings or plantlets; or (e) maize plants. In yet other embodiments of the method, the monocot plant is rice, and the explant is shoot apical meristem prepared from pre-germinated mature rice seed.

The method involves contacting an explant comprising meristem tissue of a source monocot plant with a hypertonic medium that comprises MES salt and L-proline, and that does not comprise a growth hormone, an antioxidant, silver nitrate, or a selection agent, for an amount of time sufficient to reduce turgor in the meristem tissue. In embodiments, the hypertonic medium has a higher specific osmotic pressure relative to the intercellular osmotic pressure of the meristem tissue. It will be apparent that the appropriate specific osmotic pressure depends on the length of time of contact by the explant with the hypertonic medium; the higher the osmotic pressure, the less time is necessary to achieve reduction of turgor in the meristem tissue. It is desirable to reduce turgor in the meristem tissue by at least about 20%, or by at least about 30%, e.g., between about 30% to about 60%, in comparison to a control meristem tissue that is not contacted with a hypertonic medium (e.g., instead contacted with isotonic medium). In embodiments, the contacting of the explant with the hypertonic medium is carried out for at least about 1 hour, e.g., at least about 1 hour; at least about 2 hours; about 3 hours, about 4 hours, between about 3 to about 12 hours; between about 4 to about 8 hours, about 24 hours. In addition to reducing turgor, contacting the explant with the hypertonic medium can also browning of the explant. Embodiments of hypertonic media are provided in the working Examples. Embodiments of hypertonic medium include a liquid or gel or solid; in many instances it is convenient to provide the hypertonic medium as a gel or solid onto which explants may be stably positioned for the bombardment step.

The method involves a step of bombarding the meristem tissue with transformation carriers complexed with at least one transformation agent, wherein the transformation carriers are delivered: (i) at between about 60-about 400 psi with a hand-held biolistic particle delivery system at atmospheric pressure, or (ii) using a rupture disk of less than 1100 psi with a benchtop biolistic particle delivery system under vacuum. In many embodiments, the bombarding is performed only once on the explant, thereby resulting in less potential damage of the explant (in comparison to multiple bombardments of a given explant) and overall increased viability.

In embodiments, the transformation carriers are delivered using between about 200 to about 400 psi with a hand-held biolistic particle delivery system (e.g., Helios® gene gun, Bio-Rad, Hercules, Calif.) at atmospheric pressure. In embodiments, the transformation carriers are delivered using about 200 psi, about 250 psi, about 300 psi, or about 400 psi with a hand-held biolistic particle delivery system. Alternatively, the transformation carriers are delivered using a rupture disk of less than 1100 psi (e.g., a rupture disk of 650 psi or 900 psi) with a benchtop biolistic particle delivery system (e.g., PDS-1000/He™, Bio-Rad, Hercules, Calif.) under a vacuum pressure of between about 27 to about 30 mm Hg, and with a target distance of between about 3 to about 6 centimeters.

The transformation carrier can include various materials or combinations of materials, such as carbon, silicon, silicon carbide, gold, tungsten, polymers, or ceramics, and can be provided various size ranges and shapes. In embodiments, the transformation carrier is one or more selected from the group consisting of microparticles, nanoparticles, nanowires, and nanotubes. In embodiments, the transformation carrier includes microparticles or nanoparticles of metals (e.g., gold, silver, tungsten, palladium, platinum, iridium, iron, cerium), ceramics (e.g., aluminum oxide, silicon carbide, silicon nitride, tungsten carbide), polymers (e.g., polystyrene, polydiacetylene, and poly(3,4-ethylenedioxythiophene) hydrate), semiconductors (e.g., quantum dots), silicon (e.g., silicon carbide), carbon (e.g., graphite, graphene, graphene oxide, or carbon nanosheets, nanocomplexes, or nanotubes), and composites (e.g., polyvinylcarbazole/graphene, polystyrene/graphene, platinum/graphene, palladium/graphene nanocomposites), or combinations thereof. In embodiments, the transformation carrier includes microparticles or nanoparticles that are spherical, irregular, or in the shape of wires, tubes, needles, or grids, or combinations thereof. In embodiments, the transformation carrier is a magnetic microparticle or nanoparticle (e.g., silenceMag Magnetotransfection™ agent, OZ Biosciences, San Diego, Calif.). In embodiments, the transformation carrier is covalently or non-covalently functionalized, or further includes modifiers or cross-linked materials such as polymers (e.g., linear or branched polyethylenimine, polylysine), polynucleotides (e.g., DNA or RNA), polysaccharides, lipids, polyglycols (e.g., polyethylene glycol, thiolated polyethylene glycol), polypeptides or proteins, and detectable labels (e.g., a fluorophore, an antigen, an antibody, or a quantum dot). In embodiments, transformation carrier is neutral, or carries a positive charge, or carries a negative charge. For example, one embodiment includes a charge-modified sequence-specific nuclease complexed to a transformation carrier including a charge-modified gold nanoparticle wherein the complexation is non-covalent, e.g., through ionic or electrostatic interactions. In embodiments, the transformation carrier includes nanoparticles affixed to a surface or support, e.g., an array of nanotubes or nanowires or nanoneedles vertically aligned on a substrate. Generally, the transformation carriers are delivered by a Biolistic-type technique. The size of the particles used in Biolistics is generally in the "microparticle" or "nanoparticle" range, for example, gold microcarriers in the 0.6, 1.0, and 1.6 micrometer size ranges (see, e.g., instruction manual for the Helios® Gene Gun System, Bio-Rad, Hercules, Calif.; Randolph-Anderson et al. (2015) "Sub-micron gold particles are superior to larger particles for efficient Biolistic® transformation of organelles and some cell types", Bio-Rad US/EG Bulletin 2015; O'Brian and Lummis (2011) *BMC Biotechnol.*, 11:66-71). Thus, embodiments of transformation carrier include nanoparticles, which are generally in the nanometer (nm) size range or less than 1 micrometer, e.g., with a diameter of less than about 1 nm, less than about 3 nm, less than about 5 nm, less than about 10 nm, less than about 20 nm, less than about 40 nm, less than about 60 nm, less than about 80 nm, and less than about 100 nm. Specific, non-limiting embodiments of nanoparticles commercially available (all from Sigma-Aldrich Corp., St. Louis, Mo.) include gold nanoparticles with diameters of 5, 10, or 15 nm; silver nanoparticles with particle sizes of 10, 20, 40, 60, or 100 nm; palladium "nanopowder" of less than 25 nm particle size; single-, double-, and multi-walled carbon nanotubes, e.g., with diameters of 0.7-1.1, 1.3-2.3, 0.7-0.9, or 0.7-1.3 nm, or with nanotube bundle dimensions of 2-10 nm by 1-5 micrometers, 6-9 nm by 5 micrometers, 7-15 nm by 0.5-10 micrometers, 7-12 nm by 0.5-10 micrometers, 110-170 nm by 5-9 micrometers, 6-13 nm by 2.5-20 micrometers. Embodiments of transformation carriers include materials such as gold, silicon, cerium, or carbon, e.g., gold or gold-coated nanoparticles, silicon carbide whiskers, carborundum, porous silica nanoparticles, gelatin/silica nanoparticles, nanoceria or cerium oxide nanoparticles (CNPs), carbon nanotubes (CNTs) such as single-, double-, or multi-walled carbon nanotubes and their chemically functionalized versions (e.g., carbon nanotubes functionalized with amide, amino, carboxylic acid, sulfonic acid, or polyethylene glycol moeities), and graphene or graphene oxide or graphene complexes; see, for example, Wong et al. (2016) *Nano Lett.,* 16:1161-1172; Giraldo et al. (2014) *Nature Materials,* 13:400-409; Shen et al. (2012) *Theranostics,* 2:283-294; Kim et al. (2011) *Bioconjugate Chem.,* 22:2558-2567; Wang et al. (2010) *J. Am. Chem. Soc.* Comm., 132:9274-9276; Zhao et al. (2016) *Nanoscale Res. Lett.,* 11:195-203; and Choi et al. (2016) *J. Controlled Release,* 235:222-235. See also, for example, the various types of particles and nanoparticles, their preparation, and methods for their use, e.g., in delivering polynucleotides and polypeptides to cells, disclosed in US Patent Application Publications 2010/0311168, 2012/0023619, 2012/0244569, 2013/0145488, 2013/0185823, 2014/0096284, 2015/0040268, 2015/0047074, and 2015/0208663, all of which are incorporated herein by reference in their entirety. In specific embodiments, the transformation carrier includes a particle of between about 40 nanometers to about 1.5 micrometers, e.g., a gold nanoparticle of about 0.4 to about 0.8 micrometers diameter.

The transformation carrier is complexed with at least one transformation agent. Suitable transformation agents include polynucleotides (e.g., DNA plasmids, DNA including left border and right border T-DNA sequences, DNA or RNA encoding an endonuclease such as a zinc-finger nuclease, a transcription activator-like effector "TALE" nucleases, or an RNA-guided nuclease such as CRISPR Cas nucleases, guide RNAs, and donor polynucleotides encoding a sequence to be integrated in a genome by HDR or by NHEJ), polypeptides (e.g., an endonuclease such as a zinc-finger nuclease, a transcription activator-like effector "TALE" nucleases, or an RNA-guided nuclease such as CRISPR Cas nucleases), and combinations thereof (e.g., a ribonucleoprotein including an RNA-guided nuclease and a guide RNA, optionally including a donor polynucleotide). Non-limiting embodiments of transformation agents include CRISPR Cas9 nucleases (or polynucleotides encoding Cas9 nucleases) and CRISPR Cas12a nucleases (or polynucleotides encoding Cas12a nucleases). Polynucleotides and polypeptides can be chemically modified, for example, a polypeptide such as an endonuclease (e.g., Cas9 or Cas12a) can include a cell-penetrating peptide, a nuclear localization signal peptide, a chloroplast transit peptide, or a mitochondrial targeting peptide. Transformation agents and transformation carriers can optionally be modified, e.g., by charge modification or by addition of functional moieties, to improve delivery and transformation efficiencies. In embodiments, the transformation agent includes (a) an RNA-guided nuclease or DNA or mRNA encoding an RNA-guided nuclease; (b) guide RNAs or DNA or mRNA encoding guide RNAs; and (c) at least one donor polynucleotide. In embodiments, the transformation agent includes a ribonucleoprotein comprising (a) an RNA-guided nuclease such as a Cas nuclease; (b) one or more guide RNAs; and, optionally, (c) at least one donor polynucleotide.

The method involves a step of contacting the bombarded monocot meristem tissue with a hypertonic medium, for at least about 4 hours. This step is carried out immediately after bombardment, and in embodiments, the contacting of the explant with the hypertonic medium is carried out for more than about 4 hours, e.g., about 5 hours, about 6 hours, about 7 hours, about 8 hours, between about 5 to about 12 hours, between about 6 to about 12 hours, between about 6 to about 24 hours; about 18 hours, about 24 hours, about 30 hours, or about 36 hours. In this step, the hypertonic medium can be the same as, or different from, the hypertonic medium that is used in the pre-bombardment step. For convenience, in embodiments, the hypertonic medium that is used in the immediate post-bombardment step is the same as the hypertonic medium used in the pre-bombardment step. In any case, the hypertonic medium that is used in the immediate post-bombardment step includes MES salt and L-proline but does not include any of a number of components that are frequently used in plant tissue culture, such as a growth hormone, an antioxidant, silver nitrate, or a selection agent.

Plantlets are then regenerated directly from the bombarded explant, on a base medium that does not include a growth hormone, an antioxidant, silver nitrate, or a selection agent, and without transition through a callus phase. A transformed monocot plant or plantlet that includes germline cells having multiple genetic modifications effected by the transformation agent is thus regenerated without the use of a selection agent and without transition through a callus phase.

In embodiments of the method, transformation efficiency (i.e., the number of surviving explants exhibiting at least one transformed cell or area, divided by the total number of explants subjected to bombardment, expressed as a percentage) is at least 90%, e.g., at least 90%, at least 92%, at least 94%, at least 95%, at least 97%, or at least 99%.

In specific embodiments of the method, the monocot plant is wheat, the explant includes embryonic shoot apical meristem prepared from mature wheat seed that has been subjected to imbibition, the shoot apical meristem is continuously hydrated and is made accessible for bombardment by removal of all embryonic leaf material, the explant is bombarded a single time with gold nanoparticles complexed with transfection material including an RNA-guided nuclease or mRNA encoding an RNA-guided nuclease, and the transformation carriers are delivered using a rupture disk of 650 psi or 900 psi with a benchtop biolistic particle delivery system under a vacuum pressure of between about 27 to about 30 mm Hg, and with a target distance of between about 3 to about 6 centimeters. In embodiments, the transfection material includes an RNA-guided nuclease and at least one guide RNA, and optionally includes at least one donor polynucleotide.

In specific embodiments of the method, the monocot plant is wheat, the explant includes embryonic shoot apical meristem prepared from mature wheat seed that has been subjected to imbibition, the shoot apical meristem is continuously hydrated and is made accessible for bombardment by removal of all embryonic leaf material, the explant is bombarded a single time with gold nanoparticles complexed with transfection material including an RNA-guided nuclease or mRNA encoding an RNA-guided nuclease, and the transfection carriers are delivered using between about 60-about 400 psi with a hand-held biolistic particle delivery system at atmospheric pressure, and with a target distance of between about 3 to about 6 centimeters. In embodiments, the transfection material includes an RNA-guided nuclease and at least one guide RNA, and optionally includes at least one donor polynucleotide.

In embodiments of the method, the regenerated transformed ("T0") monocot plant is fertile. In embodiments, the method provides a regenerated transformed ("T0") monocot plant containing at least one genetic modification effected by the transformation agent that is absent in the source monocot plant; depending on the transformation agents used, the genetic modification can be variously characterized as transient transformation, stable genomic changes, gene editing (genome editing), base editing; single or multiplexed genetic changes. In embodiments of the method, the transformation agent includes an RNA-guided nuclease, and the T0 plant contains a genome that has been edited by the RNA-guided nuclease; examples of such "genome edits" include deletion of one or more nucleotides, insertion of one or more nucleotides, insertion of a nucleotide sequence encoded by a donor polynucleotide, allele substitution or replacement, and combinations of such genomic changes. In embodiments, the regenerated transformed T0 monocot plant has a genome that is greater than 99.9% identical to that of the source monocot plant. Because the method does not require tissue culture through a callus phase, the T0 plant (and progeny T1 seeds or T1 plants) do not exhibit the degree of epigenetic changes (such as hypomethylation) that is observed in transformed plants that are produced using tissue culture through a callus phase. In embodiments, the genome of a regenerated stably transformed T0 monocot plant (and progeny T1 seeds or T1 plants) differs significantly from the genome of a plant obtained by traditional breeding (i.e., crossing of a male parent plant and a female parent plant), where unwanted and random exchange of genomic regions as well as random mitotically or meiotically generated genetic and epigenetic changes in the genome typically occurs during the cross and are then found in the progeny plants. Thus, in embodiments, the genome of a stably transformed T0 plant or T1 seeds or plants is more than 99.9% identical to the genome of the source monocot plant. In embodiments, the genome of a stably transformed T0 plant or T1 seeds or plants is devoid of random mitotically or meiotically generated genetic or epigenetic changes relative to the genome of the source monocot plant. In embodiments, the genome of a stably transformed T0 plant or T1 seeds or plants includes a difference of epigenetic changes in less than 0.01% of the genome relative to the genome of the source monocot plant. In embodiments, the genome of a stably transformed T0 plant or T1 seeds or plants includes: (a) a difference of DNA methylation in less than 0.01% of the genome, relative to the genome of the source monocot plant; or (b) a difference of DNA methylation in less than 0.005% of the genome, relative to the genome of the source monocot plant; or (c) a difference of DNA methylation in less than 0.001% of the genome, relative to the genome of the source monocot plant. In embodiments, a gene of interest located on a given chromosome in cells of the monocot plant is specifically targeted for editing or mutation (e.g. using a sequence-specific nuclease such as a CRISPR nuclease), and the genome of the resulting stably transformed T0 plant or T1 seeds or plants includes: (a) a difference of DNA methylation in less than 0.01% of the portion of the genome that is contained within the chromosome containing the gene of interest, relative to the genome of the source monocot plant; or (b) a difference of DNA methylation in less than 0.005% of the portion of the genome that is contained within the chromosome containing the gene of interest, relative to the genome of the source monocot plant; or (c) a difference of DNA methylation in less than 0.001% of the portion of the genome that is contained within the chromosome containing the gene of interest, relative to the genome of the source monocot plant. In embodiments, the genome of a stably transformed T0 plant or T1 seeds or plants has not more unintended changes in comparison to the genome of the source monocot plant than $1 \times 10^{-8}$ mutations per base pair per replication.

In embodiments, the method further includes the step of recovering T1 seeds from the transformed T0 monocot plant, wherein the T1 seeds obtained from a single transformed monocot plant individually include one of at least two T1 genomes that differ from each other in their genetic modifications, relative to the genome of the source monocot plant. In embodiments, a single transformed explant yields transformed germline cells (e.g., from the L2 layer of a shoot apical meristem) having multiple heritable genetic modifications effected by the transformation agent(s). For example, a single transformed wheat, rice, or maize explant provides a transformed T0 plant that yields a multiplicity of seeds, wherein the seeds individually include at least one of two or more T1 genomes that differ from each other in their genetic modifications, relative to the genome of the source monocot plant.

In embodiments, the method further includes the step growing a progeny ("T1") transformed monocot plant from the T1 seed. In embodiments, the method provides a transformed T1 monocot plant containing at least one genetic modification effected by the transformation agent on the explant and resulting T0 plant that is absent in the source monocot plant; depending on the transformation agents used, the genetic modification can be variously characterized as transient transformation, stable genomic changes, gene editing (genome editing), base editing; single or multiplexed genetic changes. In embodiments of the method, the transformation agent includes an RNA-guided nuclease, and the T1 plant contains a genome edit resulting from the effects of the RNA-guided nuclease on the explant and resulting T0 plant; examples of such "genome edits" include deletion of one or more nucleotides, insertion of one or more nucleotides, insertion of a nucleotide sequence encoded by a donor polynucleotide, allele substitution or replacement, and combinations of such genomic changes. In embodiments, the transformed T1 monocot plant has a genome that is greater than 99.9% identical to that of the source monocot plant. Because the method does not require tissue culture through a callus phase, the transformed T1 monocot plant does not exhibit the degree of epigenetic changes (such as hypomethylation) that is observed in transformed plants that are produced using tissue culture through a callus phase. Thus, a further aspect of the invention is related to a transiently or stably transformed T0 monocot plant produced by the method. Another aspect of the invention is related to transformed T1 seed or transformed T1 progeny plants produced by the method.

The above-described method improves on transformation technology by reducing the physical stress on the explant or meristem cells that are subjected to the transformation procedures, by including a pre-bombardment treatment on hyperosmotic medium, an immediately post-bombardment treatment on hyperosmotic medium to improve survival of the transformed meristematic cells, use of only a single bombardment "shot", and bombarding at relatively lower pressures than typically employed. This improvements result in high viability (typically near 100%) of the transformed explants, higher overall transformation efficiency (in terms of the number of transformed explants relative to the total number of explants subjected to the transformation procedure, which is typically at least 90%), and higher transformation efficiency in terms of the total number of transformed meristem cells in a given explant (as indicated by a large number of transformed L2 cells in a shoot apical meristem). In particular, the high transformation efficiency in terms of the total number of transformed L2 cells in a given explant is expected to result in the production of multiple independent transformation "events" (individual genetic changes or mutations) in a single explant; this allows performance of a saturated targeted editing or targeted mutagenesis screen (e.g., using a sequence-specific endonuclease such as CRISPR-Cas), in which a range of phenotypes of one or several mutated gene combinations can be produced. High efficiency L2 cell transformation is expected to result in chimeric T0 plants. Each regenerated T0 plant thus carries many independent mutations (e.g., independent genomic changes resulting from a specific CRISPR-Cas editing target); the independent L2 mutations eventually differentiate into microspores and megaspores. Thus, it is possible that T1 seed or T1 plant populations can exhibit the entire range of phenotypes that can possibly be produced in an elite germplasm genetic background.

Related Disclosure

Plants of Interest: The method is useful in transforming monocot plants, including wheat, maize, rice, barley, millet, and sorghum. Embodiments include grain crop plants and turf grasses. Embodiments include barley (*Hordeum vulgare*), maize (*Zea mays* L.) and other *Zea* spp., millets (*Setaria* spp, *Echinochloa* spp, *Eleusine* spp, *Panicum* spp., *Pennisetum* spp.), oats (*Avena sativa*), oil palm (*Ellis quineensis*), onion (*Allium cepa*) and other *Allium* spp., bananas and plantains (*Musa* spp.), rice (*Oryza sativa* L.), rye (*Secale cereale*), sorghum (*Sorghum bicolor*), sugarcanes (*Saccharum* spp.), bread wheat (*Triticum aestivum*), spelt (*Triticum spelta*), emmer (*Triticum dicoccum*), einkorn (*Triticum monococcum*), durum wheat (*Triticum turgidum* or *Triticum durum*), and synthetic hexaploid wheat.

Vectors: Plasmids designed for use in plants and encoding CRISPR genome editing elements (CRISPR nucleases and guide RNAs) are publicly available from plasmid repositories such as Addgene (Cambridge, Mass.; also see "addgene [dot]com") or can be designed using publicly disclosed sequences, e. g., sequences of CRISPR nucleases. In embodiments, such plasmids are used to co-express both a CRISPR nuclease mRNA and guide RNA(s); in other embodiments, a CRISPR nuclease mRNA and guide RNA are encoded on separate plasmids. In embodiments, the plasmids are *Agrobacterium* TI plasmids. Materials and methods for preparing expression cassettes and vectors for CRISPR endonuclease and guide RNA for stably integrated and/or transient plant transformation are disclosed in PCT/US2015/018104 (published as WO/2015/131101 and claiming priority to U.S. Provisional Patent Application 61/945,700), US Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, such expression cassettes are isolated linear fragments, or are part of a larger construct that includes bacterial replication elements and selectable markers; such embodiments are useful, e. g., for particle bombardment or nanoparticle delivery or protoplast transformation. In embodiments, the expression cassette is adjacent to or located between T-DNA borders or contained within a binary vector, e. g., for *Agrobacterium*-mediated transformation. In embodiments, a plasmid encoding a CRISPR nuclease is delivered to a cell (such as a plant cell or a plant protoplast) for stable integration of the CRISPR nuclease into the genome of the cell, or alternatively for transient expression of the CRISPR nuclease. In embodiments, plasmids encoding a CRISPR nuclease are delivered to a plant cell or a plant protoplast to achieve stable or transient expression of the CRISPR nuclease, and one or multiple guide RNAs (such as a library of individual guide RNAs or multiple pooled guide RNAs) or plasmids encoding the guide RNAs are delivered to the plant cell or plant protoplast individually or in combinations, thus providing libraries or arrays of plant cells or plant protoplasts (or of plant callus or whole plants derived therefrom), in which a variety of genome edits are provided by the different guide RNAs.

EXAMPLES

Example 1

This example illustrates several embodiments of media useful in the methods described herein, which include the step of contacting an explant including meristem tissue of a source monocot plant with a hypertonic medium. More specifically, this example provides recipes for a hypertonic ("osmotic") medium that includes MES salt and L-proline, and that does not include a growth hormone, an antioxidant, silver nitrate, or a selection agent, and that is employed in the pre-bombardment step, during which the explant to be bombarded is contacted with a liquid, gel, or solid "osmotic" or hypertonic medium for an amount of time sufficient to reduce turgor in the meristem tissue. This medium is further employed in the immediate post-bombardment step of the method.

Table 1 provides non-limiting examples of hypertonic media formulations that are suited for use in the pre-bombardment and immediate post-bombardment steps, and illustrate suitable ranges of various components. The components and amounts required to make the base medium are listed (quantities given are for 1 liter of medium). Final pH values are also provided. The formulations as provided do not list optional gelling or solidifying agents, which may be included using standard media formulation procedures as described below; suitable gelling or solidifying agents include Gelrite (catalogue number G35020, Research Products International, Mt. Prospect, Ill.) and Phytagel (P8169, Sigma, St. Louis, Mo.). To prepare 1 litre of medium, add appropriate amount of each component to 800 mL of distilled or deionized water and place on a magnetic stirrer until all components are fully dissolved. Measure pH and add distilled water to make volume up to 1 L. Autoclave at 121 degrees Celsius for 25 minutes. Cool medium to 60 degrees Celsius and pour into petri plates (100 mm×25 mm) under sterile conditions. Allow plates to dry and store at room temperature for up to 2 weeks, or at 4 degrees Celsius for up to 6 weeks.

TABLE 1

Hypertonic Media*

| Component (source) | Amount for 1 L medium | Hypertonic Medium Formula 1 | Hypertonic Medium Formula 2 | Hypertonic Medium Formula 3 | Hypertonic Medium Formula 4 |
|---|---|---|---|---|---|
| MS medium (M519, Phytotech Laboratories, Lenexa, KS) | 4.0-4.7 g | 4.3 g | 4.3 g | 4.3 g | 4.3 g |
| Sucrose (S8501, Sigma, St. Louis, MO) | 20-40 g | 30 g | 30 g | 30 g | 30 g |
| Sorbitol (S1876, Sigma, St. Louis, MO) | 20-40 g | 25 g | 25 g | 37 g | 25 g |
| Mannitol (M4125, Sigma, St. Louis, MO) | 20-40 g | 25 g | 25 g | 37 g | 25 g |
| L-Proline (P5607, Sigma, St. Louis, MO) | 0.4-1.2 g | 0.5 g | 0.5 g | 0.5 g | 0.5 g |
| MES (M3671, Sigma, St. Louis, MO) | 0.6-1.2 g | 1.2 g | 1.2 g | 0.8 g | 1.2 g |
| myo-inositol (I7508, Sigma, St. Louis, MO) | 90-150 mg | 150 g | 125 g | 113 g | 90 g |
| pH adjusted to | — | 5.8 | 5.8 | 5.7 | 5.7 |

*all amounts provided to make 1 L total volume

Example 2

This example illustrates several embodiments of media useful in the methods described herein. More specifically, this example provides recipes for a base medium that includes MES salt and L-proline, and that does not include a growth hormone, an antioxidant, silver nitrate, or a selection agent, and that is employed in the plant regeneration step of the method.

Table 2 provides non-limiting examples of base media formulations that are suited for use in the plant regeneration step, and illustrate suitable ranges of various components. The components and amounts required to make the base medium are listed (quantities given are for 1 liter of medium). Final pH values are also provided. The formulations as provided do not list optional gelling or solidifying agents, which may be included using standard media formulation procedures as described below; suitable gelling or solidifying agents include Gelrite (catalogue number G35020, Research Products International, Mt. Prospect, Ill.) and Phytagel (P8169, Sigma, St. Louis, Mo.). To prepare 1 litre of medium, add appropriate amount of each component to 800 mL of distilled or deionized water and place on a magnetic stirrer until all components are fully dissolved. Measure pH and add distilled water to make volume up to 1 L. Autoclave at 121 degrees Celsius for 25 minutes. Cool medium to 60 degrees Celsius and pour into petri plates (100 mm×25 mm) under sterile conditions. Allow plates to dry and store at room temperature for up to 2 weeks, or at 4 degrees Celsius for up to 6 weeks.

TABLE 2

Base Medium*

| Component | Amount for 1 L medium | Base Medium Formula 1 | Base Medium Formula 2 | Base Medium Formula 3 | Base Medium Formula 4 |
|---|---|---|---|---|---|
| MS medium (M519, Phytotech Laboratories, Lenexa, KS) | 4.0-4.7 g | 4.5 g | 4.6 g | 4.3 g | 4.5 g |
| Sucrose (S8501, Sigma, St. Louis, MO) | 20-40 g | 30 g | 30 g | 30 g | 30 g |
| L-Proline (P5607, Sigma, St. Louis, MO) | 0.4-1.2 g | 0.5 g | 0.5 g | 0.7 g | 1.2 g |
| MES (M3671, Sigma, St. Louis, MO) | 0.6-1.2 g | 1.2 g | 0.7 g | 0.6 g | 1.0 g |
| myo-inositol (I7508, Sigma, St. Louis, MO) | 90-150 mg | 120 mg | 120 mg | 109 mg | 100 mg |
| pH adjusted to | — | 5.8 | 5.8 | 5.8 | 5.8 |

*all amounts provided to make 1 L

Example 3

This illustrates non-limiting embodiments of the method of providing a transformed monocot plant, the method including the steps of: (a) contacting an explant including meristem tissue of a source monocot plant with a hypertonic medium for an amount of time sufficient to reduce turgor in the meristem tissue; (b) bombarding the meristem tissue with transformation carriers complexed with at least one transformation agent, wherein the transformation carriers are delivered: (i) at between about 60-about 400 psi with a hand-held biolistic particle delivery system at atmospheric pressure, or (ii) using a rupture disk of less than 1100 psi with a benchtop biolistic particle delivery system under vacuum; (c) contacting the bombarded monocot meristem tissue with the hypertonic medium for at least about 4 hours; and (d) regenerating plantlets without transition through a callus phase; whereby a transformed monocot plant that includes germline cells having multiple genetic modifications effected by the transformation agent is regenerated without the use of a selection agent and without transition through a callus phase. More specifically, this example illustrates use of these compositions and methods to provide transformed wheat plants at high transformation efficiencies, without the use of a selection agent and without transition through a callus phase. These methods are useful for bread wheat (*Triticum aestivum*), spelt (*Triticum spelta*), emmer (*Triticum dicoccum*), einkorn (*Triticum monococcum*), durum wheat (*Triticum turgidum* or *Triticum durum*), or synthetic hexaploid wheat varieties, independent of genotype or germplasm.

In this example, bread wheat (*Triticum aestivum*) cultivars "Fielder" soft white spring wheat (see: www[dot]wheatpedigree.net/sort/show/20087), "Bobwhite" spring wheat (see: wheatpedigree[dot]net/sort/show/8192), and "Glenn" hard red spring wheat (see: ndsuresearchfoundation[dot]org/glenn) are used as the source plants. Mature wheat seeds are sterilized for 20-30 minutes in a solution containing bleach (50%+1 drop Tween 20) and rinsed several times with autoclaved deionized water. Sterilized seeds are arranged on moist filter paper with the embryo side facing up and incubated at 26 degrees Celsius in the dark for about 24 to 36 hours. Embryos are excised from the imbibed seeds, by nudging the embryo on either side with the blunt end of a sterile scalpel to detach it from the endosperm. Isolated embryos are immediately transferred to sterile distilled water or liquid hypertonic ("osmotic") medium (see Example 1); embryos and the later dissected explants are kept continually hydrated by contact with or submersion in liquid. For meristem dissection, about 0.3 mm of the coleoptile covering the shoot apical meristem is removed with a sterile scalpel under a stereomicroscope. Surrounding leaf layers around the meristem are also removed using an insulin needle to further expose the meristem. The prepared meristem explants are incubated in hypertonic medium for between about 2 to about 6 hours, or a period of time sufficient to reduce turgor in the explants; this treatment also prevents browning of the explants. The explants are then arranged in an approximately 5×5 square grid pattern within a 2.5-cm diameter target circle in the center of a petri plate containing solid base medium (see Example 2).

Transformation carriers employed are gold nanoparticles of between about 40 nanometers to about 1.5 micrometers, which are prepared, e.g., according to the gold nanoparticles manufacturer's recommendations. The transformation carrier is complexed with at least one transformation agent, such as one or more polynucleotides, polypeptides, or a combination thereof (such as a ribonucleoprotein including an endonuclease). In one experiment, plasmids encoding either a green fluorescent protein (GFP) reporter gene or a red fluorescent protein (RFP) reporter gene are added to 600 nm gold particles (2.5 micrograms of DNA added to 25 microliters "lx" gold nanoparticles, 40 milligrams/milliliter) and mixed by gently pipetting up and down. Calcium chloride (25 microliters of 2.5 M $CaCl_2$) and 10 microliters 200 millimolar spermidine are added to the mixture, which is then incubated on a shaking vortex for 10-20 minutes. The gold:DNA mixture is allowed to settle for 5-10 minutes at room temperature and then pelleted by centrifugation at 3000 rpm for 30-60 seconds. The supernatant is removed by pipetting. The pellet is resuspended in 250 microliters ice-cold absolute ethanol and the gold nanoparticles allowed to settle for 5-10 minutes at room temperature. The mixture is centrifuged again at 3000 rpm for 30-60 seconds and the supernatant is removed by pipetting. The pellet is resuspended in 65 microliters ice-cold absolute ethanol. This volume is sufficient for 5 biolistics "shots". Bombardment of the wheat meristem explants is performed using the Bio-Rad PDS-1000/He "gene gun" (benchtop biolistic particle delivery system, Bio-Rad, Hercules, Calif.), operated according to the manufacturer's instructions; see www[dot]bio-rad[dot]com/en-us/product/pds-1000-he-hepta-systems. The following parameters are used: 650 psi, 900 psi, or 1100 psi rupture disks (each rupture disk loaded with up to 13 microliters of prepared gold nanoparticles); target distance of about 3 to about 6 centimeters; and vacuum pressure of about 27 to about 30 mm Hg. Each plate containing 25 explants in a grid pattern is bombarded with a single "shot" of the prepared gold nanoparticles. Alternatively bombardment of the wheat meristem explants is performed using the Bio-Rad PDS-1000/He "gene gun" (benchtop biolistic particle delivery system, Bio-Rad, Hercules, Calif.), operated according to the manufacturer's instructions; see www[dot]bio-rad[dot]com/en-us/product/pds-1000-he-hepta-systems. The following parameters are used: 650 psi, 900 psi, or 1100 psi rupture disks (each rupture disk loaded with up to 13 (e.g., up to 10) microliters of prepared gold nanoparticles); target distance of about 3 to about 6 centimeters; and vacuum pressure of about 27 to about 30 mm Hg. Each plate containing 25 explants in a grid pattern is bombarded with a single "shot" of the prepared gold nanoparticles. Alternatively, bombardment of the wheat meristem explants is performed using the Bio-Rad Helios® Gene Gun System (hand-held biolistic particle delivery system, Bio-Rad, Hercules, Calif.), operated according to the manufacturer's instructions; see www[dot]bio-rad[dot]com/en-us/product/helios-gene-gun-system. The following parameters are used: prepared gold nanoparticles loaded into cartridges are bombarded using between about 200 to about 400 psi (e.g., at 200 psi, 250 psi, 300 psi, or 400 psi) onto the prepared explants at atmospheric pressure. Each plate containing 25 explants in a grid pattern is bombarded with a single "shot" of the prepared gold nanoparticles.

After bombardment, the explants are transferred to fresh plates of hypertonic ("osmotic") medium and incubated at 26 degrees Celsius in the dark for at least about 4 hours, preferably at least about 12 hours (e.g., between about 24 to about 36 hours). At this point the explants or meristems can be screened for GFP or RFP reporter gene expression by visualizing under a fluorescence microscope.

Figure 1B:
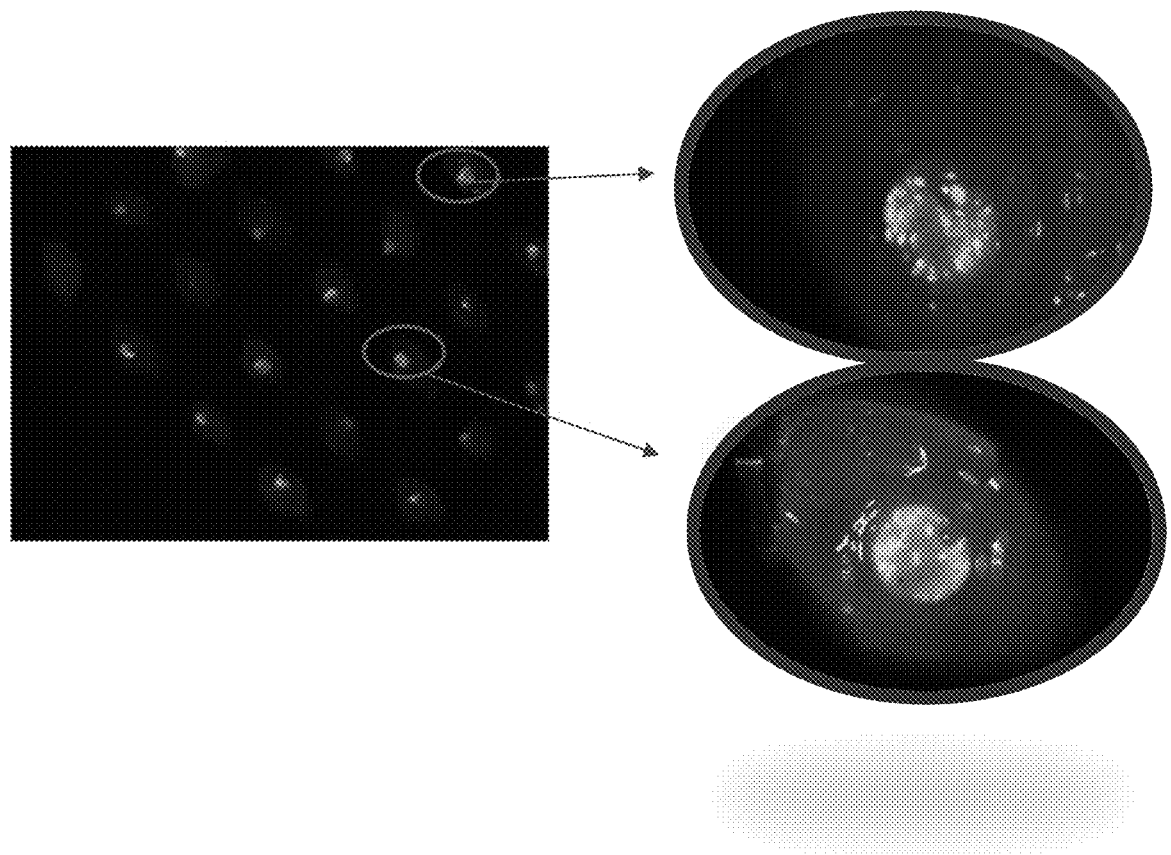
FIG. 1B, left panel is a fluorescence micrograph of the same sample pictured in FIG. 1A; all explants show GFP expression, indicating viability and successful transformation.
Figure 1C:
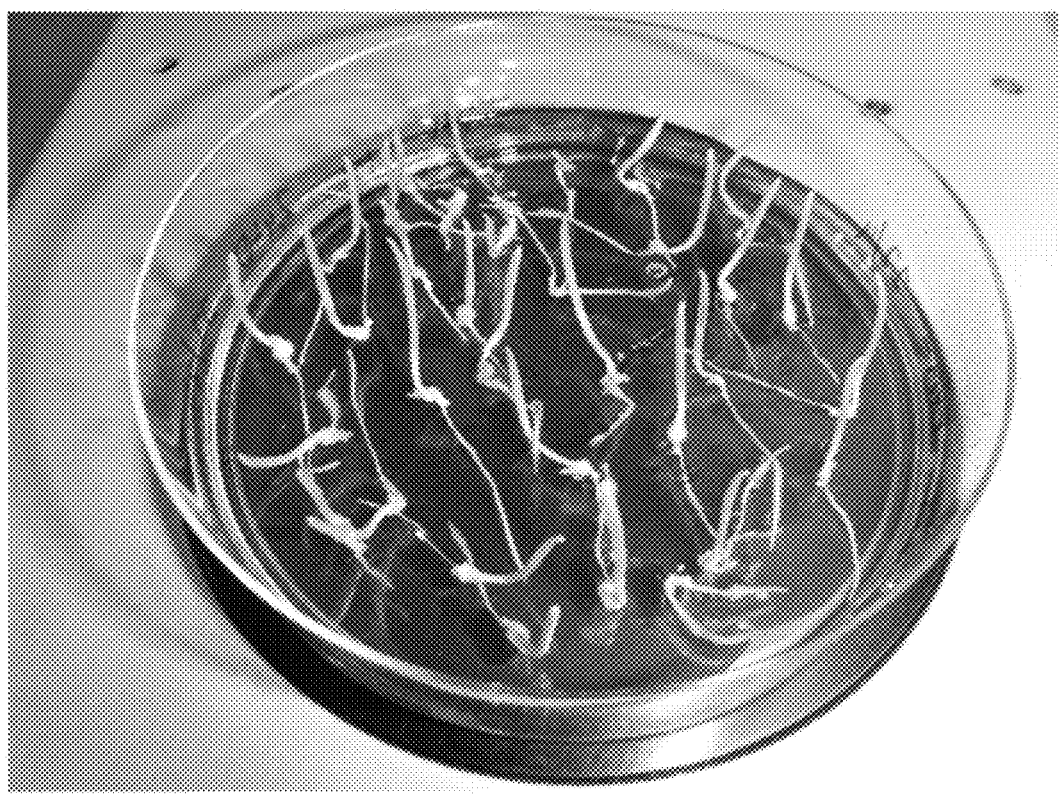
FIG. 1C illustrates a plate of wheat plantlets regenerated in a typical bombardment experiment, with virtually all explants remaining viable and developing directly into plantlets without a callus phase.

In a series of experiments following the protocols described above, wheat meristem explants are transferred to fresh plates of hypertonic ("osmotic") medium and incubated at 26 degrees Celsius in the dark for between about 24 to about 36 hours. Examination of the explants under a fluorescent microscope showed a very high percentage of the bombarded meristems displayed marker gene expression with strong intensity and excellent coverage (more than 75% surface area of the meristem) in each sample. Typical results are illustrated in FIG. 1A-1C. Results from a series of experiments are provided in Table 3.

TABLE 3

| Experiment | Number of explants bombarded (900 psi) | Number of explants with at least one spot or area of GFP expression | % | Number of explants with more than 5 spots or areas of GFP expression | % |
| --- | --- | --- | --- | --- | --- |
| 1 | 100 | 60 | 60% | 17 | 17% |
| 2 | 100 | 90 | 90% | 56 | 56% |
| 3 | 100 | 86 | 86% | 65 | 65% |
| 4 | 97 | 97 | 100% | 95 | 98% |

The procedures described above for wheat transformation are generally also applicable to many monocots, including grain crops such as maize and rice. Suitable maize (Zea mays) explants can be obtained from mature or immature maize ears as follows. Remove husks from maize ears (e.g., 9, 10, 11, or 12 days after pollination) and trim off about 2-3 centimeters from both ends of the ear. Insert a pair of forceps into the tip of the ear to serve as a handle for movement and positioning during dissection. In a laminar flow bench, place ears in a sterile, 2-L beaker and add about 1 L of sterilizing solution (50% bleach and 1 to 2 drops of Tween 20), ensuring that the ears are completely submerged. Move the ears around in the sterilizing solution 2-3 times during sterilization to dislodge air pockets and ensure thorough surface sterilization. Pour off the bleach solution after 20 minutes and rinse the ears three times using at least 800 milliliters of sterile deionized water for each rinse. After the final wash is discarded, keep the ears in a dry sterile beaker in the flow bench until dissection. Working in a laminar flow bench, place surface-sterilized ear in a large (150×15 mm) sterile Petri plate (either base or lid can be used). Using aseptic technique, and forceps as a handle, place the ear either upright or horizontal on the Petri plate, insert a surgical blade between two kernels to the point of attachment and carefully detach the kernel from the cob. Sterilize dissection tools repeatedly throughout the procedure. Holding the kernel with forceps under a stereomicroscope, excise the embryo. Transfer the excised embryo, meristem facing up, directly to a filter paper placed on one half MS media (or other appropriate media). Incubate embryos in the dark at 26 degrees Celsius for 2-6 days. To prepare explants for transformation, microdissect the meristem by carefully removing the coleoptile and leaves covering the shoot apical meristem with sterile fine-tip forceps and insulin needles to expose the meristem located at the base of the coleoptile. Transfer the meristem immediately to a petri plate containing filtered autoclaved water (or a base medium such as those in Example 2) to keep the explants hydrated. Arrange the explants on hypertonic ("osmotic") medium (see Example 1 and the wheat protocol in this example), typically with 42 explants per plate, and incubate between about 2 to about 4 hours prior to bombardment. Follow bombardment procedure, post bombardment treatment, and plant recovery (regeneration) generally as described above for wheat. In a non-limiting embodiment, maize embryonic meristem explants are bombarded with gold nanoparticles (600 nm) complexed with at least one transformation agent, e.g., a DNA plasmid encoding a reporter such as green fluorescent protein (GFP), a DNA plasmid encoding a Cas nuclease, one or more DNA plasmids encoding a guide RNA, one or more DNA plasmids encoding a donor polynucleotide encoding a nucleotide sequence for HDR-mediated integration into the genome, or a combination of any of these. In some embodiments, gold nanoparticles complexed with a polynucleotide transformation are further combined with stabilizing agents such as calcium chloride or a polyamine (e.g., spermine, spermidine, or putrescine). In non-limiting embodiments, the mass ratio (e.g., microgram/microgram) of DNA to gold nanoparticles is about 2.5/1000, about 5/1000, about 7.5/1000, about 10/1000, or about 12.5/1000; in further non-limiting embodiments, such DNA/gold nanoparticle complexes are further combined with $CaCl_2$ (e.g., at ratios of about 25, 35, 50, 60, or 75 micromoles $CaCl_2$ per 1000 micrograms of gold) or with a polyamine such as spermidine (e.g., at ratios of about 0.25, 0.5, 0.75, 1.0, 1.5, or 2.0 micromoles polyamine per 1000 micrograms of gold). Following bombardment, the maize embryonic meristem explants are incubated on the hypertonic ("osmotic") medium overnight, and then transferred to half MS medium and incubated at 26 degrees Celsius in the dark until the first shoots appear, at which point the plate is incubated under light.

For transformation of rice (Oryza sativa or related spp.), explants are prepared from mature rice (Nipponbare) seeds as follows. Remove hulls from rice seeds and sterilize in a solution of 50% bleach with 1 drop of Tween 20 added, followed by a second sterilization in 70% ethanol for 5 minutes. Rinse seeds several times to remove traces of ethanol. Transfer up to 5 seeds into a petri plate containing one half MS media and allow the seeds to germinate in vitro until the coleoptile emerges and grows to about 1-3 inches in length; this may take about 5-9 days. To expose shoot apical meristem, remove all primordial leaves surrounding the shoot apical meristem using sterile fine-tip forceps and transfer the explant immediately to hyperosmotic medium (see Example 1 and the wheat protocol in this example) for about 2-about 4 hours prior to bombardment. Arrange 12 explants in a 3×4 grid on solid base medium (see Example 2) in a petri plate for bombardment. Bombard the explants following the procedures described above for wheat or maize. Transfer the bombarded explants to hyperosmotic medium (see Example 1) and incubate between 24-36 hours. Transfer the explants to a base medium (see Example 2) for recovery of transformed plantlets.

The above procedures are repeated with wheat, maize, or rice explants prepared as described above, and using gold nanoparticles complexed with either a ribonucleoprotein including a Cas nuclease and guide RNAs, or with polynucleotides encoding a Cas nuclease and guide RNAs. In embodiments, the transformed explants are regenerated into fertile T0 plants. T1 seeds are collected from the T0 plants. Analysis of the T1 seeds (or progeny T1 plants grown from the T1 seed) confirms that the transformed T1 seeds or progeny T1 plants have a genome that is greater than 99.9% identical to that of the source monocot plant, and is devoid of random mitotically or meiotically generated genetic or epigenetic changes relative to the genome of the source monocot plant. In embodiments, the genetic modification(s) effected by the transformation agent in the genome of T1 seeds differs between individual T1 seeds obtained from a single transformed T0 plant; in such embodiments, a single T0 plant yields a population of T1 seeds having a multiplicity of genotypes and a resulting multiplicity of phenotypes.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this invention have been described in terms of embodiments and illustrative examples, it will be apparent to those of skill in the art that substitutions and variations can be applied to the materials and methods described herein without departing from the concept, spirit, and scope of the invention. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the invention as encompassed by the embodiments of the inventions recited herein and the specification and appended claims.

What is claimed:
1. A method of providing a transformed monocot plant, the method comprising the steps of:
 (a) contacting an explant comprising meristem tissue of a source monocot plant with a hypertonic medium for at least about 2 hours to reduce turgor in the meristem tissue, wherein the hypertonic medium has a higher specific osmotic pressure relative to the intercellular osmotic pressure of the meristem tissue, and wherein the hypertonic medium comprises MES salt and L-proline and does not comprise a growth hormone, an antioxidant, silver nitrate, or a selection agent;
 (b) bombarding the meristem tissue with transformation carriers complexed with at least one transformation agent, wherein the transformation carriers comprise microparticles or nanoparticles, and wherein the transformation carriers are delivered: (i) at between about 60-about 400 psi with a hand-held biolistic particle delivery system at atmospheric pressure, or (ii) using a rupture disk of less than 1100 psi with a benchtop biolistic particle delivery system under vacuum;

(c) contacting the bombarded monocot meristem tissue with the hypertonic medium for at least about 4 hours; and (d) regenerating plantlets on a base medium that does not comprise a growth hormone, an antioxidant, silver nitrate, or a selection agent, without transition through a callus phase;

whereby a transformed monocot plant that comprises at least two germline cells having different genetic modifications effected by the transformation agent is regenerated.

2. The method of claim 1, wherein the monocot plant is: (a) from the family Poaceae (Gramineae); (b) a grain crop species; (c) selected from the group consisting of wheat, maize, rice, barley, millet, and *sorghum*; (d) selected from the group consisting of common or bread wheat (*Triticum aestivum*), spelt (*Triticum spelta*), emmer (*Triticum dicoccum*), einkorn (*Triticum monococcum*), durum wheat (*Triticum turgidum* or *Triticum durum*), or synthetic hexaploid wheat; (e) elite germplasm of a grain crop species; or (f) an inbred line of a grain crop species.

3. The method of claim 1, wherein the meristem tissue comprises: (a) shoot apical, root apical, nodal, or auxiliary meristem tissue; (b) meristem tissue in an embryo, seedling or plantlet, or plant; (c) a monocot meristem tissue that is partially or wholly accessible/exposed to bombardment; or (d) shoot apical meristem made accessible for bombardment by removal of all embryonic leaf material.

4. The method of claim 1, wherein the meristem tissue is kept continually moist.

5. The method of claim 1, wherein the monocot plant is: (a) wheat, and wherein the explant comprises embryonic shoot apical meristem prepared from mature wheat seed that has been subjected to imbibition; (b) maize, and wherein the explant comprises shoot apical meristem; or (c) rice, and wherein the explant is shoot apical meristem prepared from pre-germinated mature rice seed.

6. The method of claim 1, wherein the monocot plant is maize, and wherein the explant comprises shoot apical meristem that is prepared by microdissection of: (a) immature maize embryos, (b) mature maize embryos, (c) germinating maize embryos, (d) maize seedlings or plantlets; or (e) maize plants.

7. The method of claim 1, wherein the hypertonic medium of (a) is a liquid, and wherein the hypertonic medium of (c) is a gel or solid.

8. The method of claim 1, wherein the contacting of the explant with the hypertonic medium results in reduction of turgor in the meristem tissue by at least about 20% in comparison to a control meristem tissue that is not contacted with a hypertonic medium.

9. The method of claim 1, wherein the contacting of the explant with the hypertonic medium is carried out for between about 3 to about 12 hours to reduce turgor in the meristem tissue.

10. The method of claim 1, wherein the bombarded monocot meristem tissue is contacted with the hypertonic medium for between about 12 to about 36 hours.

11. The method of claim 1, wherein the transformation carriers are delivered using: (a) about 200 to about 400 psi with a hand-held biolistic particle delivery system at atmospheric pressure; or (b) a rupture disk of 650 psi or 900 psi with a benchtop biolistic particle delivery system under a vacuum pressure of about 27 to about 30 mm Hg, and with a target distance of about 3 to about 6 centimeters.

12. The method of claim 1, wherein the transformation carrier comprises a particle of about 40 nanometers to about 1.5 micrometers or a gold nanoparticle of about 0.4 to about 0.8 micrometers diameter.

13. The method of claim 1, wherein the transformation agent comprises: (a) DNA comprising left border and right border T-DNA sequences; (b) DNA encoding an RNA-guided nuclease; (c) mRNA encoding an RNA-guided nuclease; (d) an RNA-guided nuclease; (e) DNA encoding guide RNAs; (f) mRNA encoding guide RNAs; (g) guide RNAs; (h) a donor polynucleotide; or (i) a combination of any two or more of (a)-(h).

14. The method of claim 1, wherein the transformation agent comprises: (a) a ribonucleoprotein comprising (i) an RNA-guided nuclease; (ii) guide RNAs; and, optionally, (iii) at least one donor polynucleotide; or (b) DNA encoding a protein.

15. The method of claim 1, wherein transformation efficiency is at least 90%.

16. The method of claim 1, wherein the monocot plant is wheat, wherein the explant comprises embryonic shoot apical meristem prepared from mature wheat seed that has been subjected to imbibition, wherein the shoot apical meristem is continuously hydrated and is made accessible for bombardment by removal of all embryonic leaf material, wherein the explant is bombarded a single time with gold nanoparticles complexed with transfection material comprising an RNA-guided nuclease, or comprising DNA or mRNA encoding an RNA-guided nuclease, or comprising an RNA-guided nuclease and at least one guide RNA and optionally at least one donor polynucleotide, wherein the transformation carriers are delivered using: (a) a rupture disk of 650 psi or 900 psi with a benchtop biolistic particle delivery system under a vacuum pressure of about 27 to about 30 mm Hg, and with a target distance of about 3 to about 6 centimeters; or (b) about 60-about 400 psi with a hand-held biolistic particle delivery system at atmospheric pressure, and with a target distance of about 3 to about 6 centimeters.

17. The method of claim 1, wherein the regenerated transformed monocot plant is fertile.

18. The method of claim 1, further comprising: recovering T1 seeds from the transformed monocot plant, wherein the T1 seeds obtained from a single transformed monocot plant individually comprise one of at least two T1 genomes that differ from each other in their genetic modifications, relative to the genome of the source monocot plant; and, optionally, further comprising growing a progeny transformed monocot plant from the T1 seed.

19. The method of claim 1, wherein the regenerated transformed monocot plant has: (a) a genetic modification effected by the transformation agent that is absent in the source monocot plant; and (b) a genome that is greater than 99.9% identical to that of the source monocot plant.

20. The method of claim 1, wherein the hypertonic medium comprises MES salt, L-proline, sucrose, sorbitol, and mannitol.

\* \* \* \* \*